United States Patent [19]

Schäfer et al.

[11] Patent Number: 4,895,921

[45] Date of Patent: Jan. 23, 1990

[54] WATER SOLUBLE OR DISPERSIBLE BLOCKED POLYISOCYANATES AND A PROCESS FOR THEIR PREPARATION AND USE

[75] Inventors: Walter Schäfer, Leichlingen; Hanns P. Müller, Bergisch Gladbach; Rolf Dhein, Krefeld, all of Fed. Rep. of Germany

[73] Assignee: Bayer Aktiengesellschaft, Bayerwerk, Fed. Rep. of Germany

[21] Appl. No.: 253,179

[22] Filed: Oct. 4, 1988

[30] Foreign Application Priority Data

Oct. 17, 1987 [DE] Fed. Rep. of Germany ....... 3735198

[51] Int. Cl.⁴ ............ C08G 18/80

[52] U.S. Cl. ............ 528/45; 427/385.5; 524/840

[58] Field of Search ............ 528/45; 524/840; 427/385.5

[56] References Cited

U.S. PATENT DOCUMENTS 4,098,933 7/1978 Burkhardt et al. ............ 427/379

4,619,966 10/1986 Schafer et al. ............ 524/589

*Primary Examiner*—Maurice J. Welsh

*Attorney, Agent, or Firm*—Joseph C. Gil; Thomas W. Roy

[57] ABSTRACT

The present invention is directed to water soluble or dispersible blocked polyisocyanates which contain (a) a statistical average per molecule of at least one structural unit corresponding to the formula:

B—CO—NH— wherein B denotes a group obtainable by removal of the acidic hydrogen atom from a monofunctional blocking agent for organic isocyanates and (b) structural units corresponding to the formula $$-NH-CO-\overset{\theta}{N}-CN$$

in a quantity sufficient to ensure the solubility or dispersibility of the blocked polyisocyanate in water, the blocked polyisocyanates containing on statistical average a total of at least two structural units corresponding to the formulae (a) and (b) per molecule.

The present invention also relates to a process for the preparation of these blocked polyisocyanates and to their use in combination with water soluble or dispersible organic compounds containing at least two isocyanate-reactive groups for the production of coated substrates which are cured by heating.

8 Claims, No Drawings

WATER SOLUBLE OR DISPERSIBLE BLOCKED POLYISOCYANATES AND A PROCESS FOR THEIR PREPARATION AND USE

BACKGROUND OF THE INVENTION

1. Field of the Invention

This invention relates to novel blocked polyisocyanates which are soluble or dispersible in water and contain cyanurea anions in a chemically bound form as groups which ensure their solubility or dispersibility, to a process for the preparation of these blocked polyisocyanates and to their use in the form of a solution or dispersion in water as hardeners in two-component lacquers.

2. Description of the Prior Art

Blocked polyisocyanates which are soluble or dispersible in water are known, for example, from DE-A-2,456,469. These compounds may be used as aqueous solutions or dispersions in combination with water soluble or dispersible polyhydroxyl compounds to serve as binder components for polyurethane lacquers which are applied from the aqueous phase.

In two-component polyurethane lacquers, the "lacquer polyisocyanates+ which are used as binder components constitute the comparatively low molecular weight activator for the relatively high molecular weight polyhydroxyl compounds. In the interests of obtaining satisfactory cross-linking and high quality coatings, these activators should have an average functionality of at least 2.5, preferably at least 3.

In the process for the preparation of the known water soluble or dispersible blocked polyisocyanates, however, a significant proportion of the isocyanate groups present in the polyisocyanates used as starting material is used up by the hydrophilic modification (reaction of a proportion of the isocyanate groups with an isocyanate-reactive hydrophilic component). The cross-linking capacity of the polyisocyanates is thereby considerably reduced.

It is therefore an object of the present invention to provide water soluble or dispersible polyisocyanates in which the hydrophilic group which renders the polyisocyanates soluble or dispersible takes part in the cross-linking reaction so that it becomes incorporated in the polyisocyanates and thereby preserves their cross-linking potential.

This problem is solved by providing the blocked polyisocyanates according to the invention described below and a process for their preparation. The hydrophilic centers present in the blocked polyisocyanates according to the invention serve a double function. They ensure that the polyisocyanates are soluble or dispersible in water and also take part in the crosslinking reaction at the same time losing their hydrophilic character.

Polyisocyanates containing anionic cyanurea groups have been described in EP-A-0,185,184, but these polyisocyanates are not self-cross-linking compounds containing blocked isocyanate groups. There is no indication in this publication that the Principle of cross-linking disclosed therein could be combined with the known type of chemical cross-linking of polyhydroxyl compounds with blocked polyisocyanates as is the case when using the blocked polyisocyanates according to the invention.

SUMMARY OF THE INVENTION

The present invention is directed to water soluble or dispersible blocked polyisocyanates which contain (a) a statistical average per molecule of at least one structural unit corresponding to the formula:

B—CO—NH— wherein B denotes a group obtainable by removal of the acidic hydrogen atom from a monofrunctional blocking agent for organic isocyanates and (b) structural units corresponding to the formula

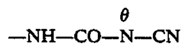

in a quantity sufficient to ensure the solubility or dispersibility of the blocked polyisocyanate in water, the blocked polyisocyanates containing on statistical average a total of at least two structural units corresponding to formulas (a) and (b) per molecule.

The present invention also relates to a process for the preparation of these blocked polyisocyanates, characterized in that organic polyisocyanates which are neither soluble nor dispersible in water are partially blocked by a known reaction with a blocking agent B—H so that the partially blocked polyisocyanate obtained contains a statistical average of at least one blocked isocyanate group per molecule in addition to free isocyanate groups, and the free isocyanate groups are then reacted in a second reaction step with a cyanamide salt of a tertiary amine or of ammonia so that anionic structural units of the formula

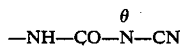

are introduced, the nature and proportions of the reactants being so chosen that the anionic structural units are present in the quantity sufficient to ensure that the products of the process will be soluble or dispersible in water.

Finally, this invention relates to the use of the water soluble or dispersible blocked polyisocyanates in the form of a solution or dispersion in water in combination with aqueous solutions or dispersions of organic compounds containing at least two isocyanate reactive groups, optionally in the presence of auxiliary agents and additives to produce surface coatings by coating suitable substrates with the combined aqueous solutions or dispersions, removing water and at the same time or subsequently cross-linking the resulting coating by heat.

DETAILED DESCRIPTION OF THE INVENTION

The following are examples of polyisocyanates which may be used as starting materials for the process according to the invention:

(i) simple organic polyisocyanates in the molecular weight range of 168 to 300, e.g. 1.6-diisocyanatohexane, 1-isocyanato-3,3,5-trimethyl-5-isocyanatomethylcyclohexane, 2,4- and/or 2,6-diisocyanatotoluene, 4,4'- and/or 2,4'-diisocyanatodiphenylmethane or 4,4'-diisocyanatodicyclohexylmethane.

These simple diisocyanates are, however, not preferred.

(ii) Modified "lacquer polyisocyanates" having an average molecular weight of up to about 1000, i.e. the modified polyisocyanates known per se based on the simple diisocyanates mentioned under (i) and modified with biuret, isocyanurate uretdione or oxadiazine trione groups. Examples include tris-(6-isocyanatohexyl)-biuret or mixtures thereof with its higher homologues, tris-(6-isocyanatohexyl)-isocyanurate or mixtures thereof with its higher homologues and optionally with bis-(6-isocyanatohexyl)-uretdione or bis-(6-iso:yanatohexyl)-oxadiazine trione.

The polyisocyanates used as starting materials for the process according to the invention preferably contain aliphatically bound isocyanate groups. Aliphatic lacquer polyisocyanates of the type exemplified under (ii) are particularly preferred starting materials.

Ionically modified, partially blocked polyisocyanates which are known from polyurethane dispersion chemistry may also be used in the process of preparation of the blocked polyisocyanates containins cyanurea anionic groups. Their use results in polyisocyanate addition products which in addition to containing the anionic structures corresponding to the above-mentioned formula also contain carboxylte or sulphonate groups. These products may be prepared from partially blocked isocyanate prepolymers which have been prepared by using hydroxyl compounds consisting entirely or partly of polyhydric alcohols containing carboxylate or sulphonate groups or by using the corresponding hydroxycarboxylic acids or hydroxysulphonic acids and then neutralizing the acid groups. The use of such anionic starting components is not preferred. First, the hydrophilic character of the anionic structural units which are essential to this invention is generally sufficient to ensure that the polyisocyanate addition products will be soluble or dispersible in water. Second, when the known anionic starting components are used, the chemically incorporated anionic groups would continue to be present in the coatings finally obtained, would fail to contribute to the cross-linking reaction and would therefore be contrary to the purpose of the invention.

The lacquer polyisocyanates exemplified under (ii) are particularly preferred starting polyisocyanates, especially the known biuret polyisocyanates and isocyanurate polyisocyanates based on 1,6-diisocyanatohexane.

Suitable blocking agents B—H for the preparation of the compounds according to the invention include in particular compounds containing an isocyanate reactive group which undergo an addition reaction with organic isocyanates at temperatures of about 20° to 120° C. to provide addition products which when mixed with non-volatile polyols containing primary hydroxyl groups will react with the non-volatile polyols at temperatures of about 100° to 200° C. to release the blocking agent and form urethane groups. Examples of suitable blocking agents include lactams such as epsilon-caprolactam, delta-valerolactam and gamma-butyrolactam; oximes such as formaldoxime, acetaldoxime, methyl ethyl ketone oxime, cyclohexanone oxime, acetophenonoxime, benzophenonoxime and diethylglyoxime; C-H-acidic compounds such as dialkylmalonates, acetylacetone and alkylacetoacetates; phenols such as phenol and o-methylphenol: imides such as phthalimide, imidazole and triazole; and secondary and tertiary alcohols such as isopropanol and tertiary butanol. Lactams, oximes, azoles and CH-acidic compounds are preferably used.

The first stage of the process according to the invention is directed to partial blocking of the isocyanate groups of the starting polyisocyanate. The quantity of blocking agent used is calculated to ensure that the resulting partially blocked polyisocyanate contains a statistical average of at least one, preferably at least two blocked isocyanate groups per molecule in addition to the free isocyanate groups which are required for the subsequent hydrophilic modification. The partially blocked polyisocyanates must contain overall statistical average of at least two free and blocked isocyanate groups. They preferably contain a total of 2.8 to 6, in particular 3 to 4 free and blocked isocyanate groups. For the hydrophilic modification of the partially blocked polyisocyanates which is carried out in the second step of the reaction, it is generally sufficient for the partially blocked polyisocyanates to contain from about 0.5 to 3.5 milliequivalents of free isocyanate groups per gram. The nature and quantitative proportions of the reactants for the second reaction step must be so chosen that the resulting anionic, blocked polyisocyanates contain a statistical average of at least one blocked isocyanate group per molecule and a total of at least two blocked isocyanate groups and anionic cyanurea groups, excluding the cation which may also contain blocked isocyanate groups. The statistical average of the sum of the two groups is preferably 2.8 to 6, in particular 3 to 4 groups per molecule and it is particularly preferred if at least two of these groups are blocked isocyanate groups. It is not essential to use equivalent quantities of the cyanamide salt in the second stage of the process, based on the number of free isocyanate groups, since any free isocyanate groups remaining will undergo a chain lengthening reaction with water when the reaction products are converted into an aqueous solution or dispersion; this reaction will not impair the usefulness of the products. The equivalent ratio of isocyanate groups to cyanurea salt in the second stage of the process is therefore generally about 1:1 to 1.5:1.

The blocking reaction is generally carried out at about 20° to 120° C. in the absence of a solvent. It is advisable to use a catalyst, which will vary with the nature of the blocking agent used. When blocking agents containing hydroxyl groups are used, it is advisable to use a metal catalyst such as dibutyl tin dilaurate; whereas, for blocking agents containing activated methylene groups, it is advisable to use basic catalysts such as diazabicyclooctane, triethylamine, alkali metal alcoholates or alkali metal phenolates such as sodium phenolate. The catalysts are used, if at all, in quantities of about 0.05 to 0.5% by weight, based on the total reaction mixture.

In the second stage of the process according to the invention, the remaining isocyanate groups of the partially blocked polyisocyanate are reacted with an ammonium salt of cyanamide to form the corresponding cyanurea salt. The reaction proceeds in accordance with the following reaction scheme:

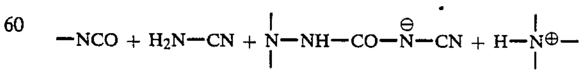

In this reaction, the components are preferably reacted together in stoichiometric quantities at reaction temperatures of about −10° to 40° C., preferably about 0° to 35° C. The salts of cyanamide may be put into the process as such or they may be prepared in situ by introducing both cyanamide and the corresponding tertiary amine at the same time. Suitable ammonium salts of cyanamide may be prepared, for example, by reacting the base with cyanamide at a temperature of about −10° to 35° C., preferably about 0° to 25° C., in an organic or aqueous medium (acetone or tetrahydrofuran are included among suitable solvents). The quantity of base is calculated to provide about 0.5 to 2 mole, preferably 1 mole of basic nitrogen atoms for each molecule of cyanamide. Analogous proportions of base and cyanamide are used for the preparation of the salts in situ.

The base from which the salt is derived may be ammonia or a tertiary amine in which preferably all the amine nitrogens are attached to aliphatic carbon atoms. The tertiary amines may contain one or more such tertiary amino groups. The preferred tertiary amines have a molecular weight of 59 to about 1000, preferably 59 to about 200. Aliphatic tertiary amines are particularly suitable, optionally containing hydroxyl groups as substituents. Examples of such tertiary amines include trimethylamine, triethylamine, tripropylamine, N,N-dimethylstearylamine, N,N-dimethylaminoethanol, N-methyl-diethanolamine and triethanolamine. It is also possible in principle to use ammonium salts of cyanamide in which the ammonium groups are based on tertiary amines containing urethane, allophanate, urea, biuret, isocyanurate, uretdione, uretoneimine, ester and/or ether groups, and especially those which contain at least two blocked isocyanate groups and correspond to the formula

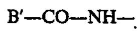

B'—CO—NH— in addition to at least one tertiary amino group. In the above formula, B' has the same meaning as B, but may be different from B.

Such modified tertiary amines may be obtained, for example, by the reaction of amino alcohols of the type exemplified above with organic polyisocyanates of the type exemplified under (i) (incorporation of urethane groups) or with isocyanate prepolymers containing allophanate, urea, biuret, isocyanurate, uretdione, uretoneimine, ester and/or ether groups. Tertiary amines containing at least two blocked isocyanate groups in addition to at least one tertiary amino group are obtained, for example, when a partially blocked isocyanate of the type exemplified above which contains at least two blocked isocyanate groups and at least one free isocyanate group is reacted with amino alcohols of the type exemplified above or with tertiary amines containing at least one primary and/or secondary amino group in addition to the tertiary amino group. N,N-dimethylethylenediamine, N,N-dimethylpropylene-diamine-(1,3) and N,N-bis-(2-aminopropyl)-methylamine are examples of these compounds.

Tertiary amines containing blocked isocyanate groups in addition to the tertiary amino groups may be prepared, for example, by reacting the polyisocyanate used as starting material (for example, a biuret polyisocyanate based on 1,6-diisocyanatohexane or an isocyanurate-containing polyisocyanate based on the same diisocyanate) with a hydroxy-functional or amino-functional tertiary amine of the type mentioned above at about 0° to 120° C. either under solvent-free tetrahydrofuran, methyl ethyl ketone or acetone). The starting compounds are used in such proportions that the resulting polyisocyanate containing tertiary amino groups will still contain a statistical average of at least two free isocyanate groups, and then reacting the free isocyanate groups still present with a stoichiometric quantity of the blocking agent B'—H at about 25° to 120° C.

The second reaction stage of the process according to the invention, i.e., reaction of the partially blocked polyisocyanates with the salts of cyanamide or with cyanamide and the corresponding base (preparation of the salts in situ) may be carried out solvent-free or in the presence of a suitable solvent. Solvents which are infinitely miscible with water and have a boiling point below 100° C. are preferably used, e.g. acetone, methyl ethyl ketone or tetrahydrofuran.

After the reaction, the product may be converted into the aqueous phase as a solution or a dispersion by stirring it into water and optionally distilling off the solvent. The quantity of water used for converting the products into aqueous solutions or dispersions is generally calculated to result in solutions or dispersions having a solids content of about 30 to 70% by weight.

If solvents of the last-mentioned type are used for the preparation of the compounds according to the invention, they may, if necessary, be removed by distillation after the aqueous solution or dispersion has been prepared. For such distillation it is advantageous for the compounds according to the invention to be resistant to hvdrolysis at a pH of 8 to 9 at the elevated temperatures employed for distillative removal of the solvent.

The resulting aqueous solutions or dispersions of the compounds according to the invention are valuable binder components, i.e. activators for aqueous coating compounds. The compounds according to the invention are particularly suitable for use as hardene s or activators for aqueous solutions or dispersions of organic compounds containing at least two isocyanate reactive groups. These include the known aqueous polyurethane dispersions which contain active hydrogen atoms for example in the form of urethane groups, aqueous polyacrylate dispersions which contain isocyanate reactive hydrogen atoms, aqueous solutions of low molecular weight polyamines containing at least two primary and/or secondary amino groups, aqueous solutions or dispersions of alkyd resins containing isocyanate reactive groups, and aqueous solutions or dispersions of organic polyhydroxyl compounds, especially polyester or polyether polyols known from polyurethane chemistry dissolved or dispersed in water. Mixtures of compounds containing isocyanate reactive groups may also be used as components to be reacted with the blocked polyisocyanates according to the invention for the preparation of aqueous coating compositions.

When the blocked polyisocyanates according to the invention are to be used according to the invention, known auxiliary agents and additives of lacquer technology such as pigments, levelling agents and fillers may be added to the blocked polyisocyanates. In addition to the blocked polyisocyanates according to the invention, the coating compounds may contain other cross-linking agents such as reactive carbonyl compounds, low molecular weight N-methylol compounds and aminoplast or phenoplast precondensates. The total quantity of cross-linking agents may vary within wide limits but must be chosen so that the degree of crosslinking finally obtained enables the coating to meet the requirements of hardness, water resistance, solvent resistance and mechanical properties.

The aqueous coating compounds which contain the blocked polyisocyanates according to the invention as the main hardening or activator components may be applied to any heat resistant substrates by any methods of coating technology. After their application, the coatings are generally cured at temperatures of about 100° to 200° C., preferably about 120° to 180° C. The process begins with evaporation of the water and any volatile tertiary amines present.

The main advantage of the blocked polyisocyanates according to the invention compared with hydrophilically modified blocked polyisocyanates known in the art lies in the fact that the heat treatment brings about not only a reaction between blocked isocyanate groups and isocyanate reactive groups, but also a condensation reaction of the anionic cyanurea group with elimination of the tertiary amine in accordance with the following reaction scheme:

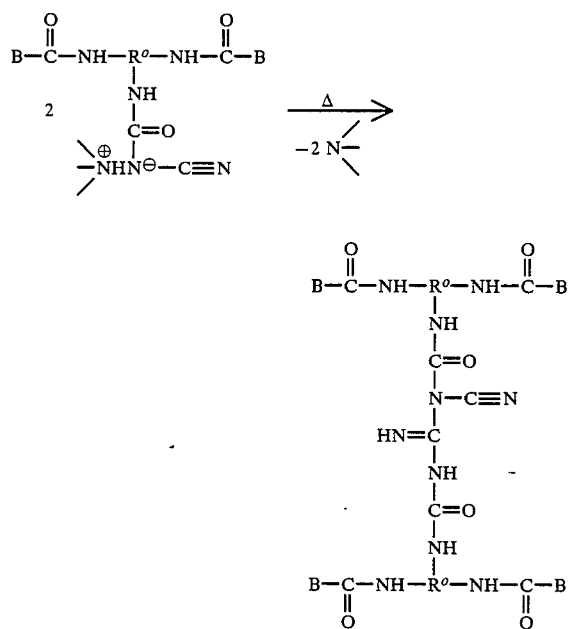

In the above formulae, B stands for the inert group of the blocking agent B—H and R° stands for the inert group of a polyisocyanate used as starting polyisocyanate.

According to this reaction scheme, the modified triisocyanate which contains two blocked isocyanate groups and one anionic cyanurea group gives rise to a blocked tetraisocyanate which acts as tetrafunctional cross-linking agent for the compounds containing isocyanate reactive hydrogen atoms. It is also possible, depending on the temperature at which the blocking agent B—H is split off, that the cross-linking reaction by which the coating is cured begins with a reaction between blocked isocyanate groups and the isocyanate reactive groups and it is only afterwards that the cross-linking reaction proceeds in accordance with the reaction scheme shown above.

It is also possible for the two cross-linking reactions to take place simultaneously. In all these cases the anionic group takes part in the cross-linking reaction with loss of its hydrophilic character in contrast to the modification of the hydrophilically modified blocked polyisocyanates known in the art. Thus, the anionic modification of the blocked polyisocyanates according to the invention does not impair the cross-linking potential of the blocked polyisocyanates.

When the blocked polyisocyanates according to the invention are based on volatile tertiary amines, the tertiary amines escape during the cross-linking process. However, when the blocked polyisocyanates according to the invention are based on difficultly volatile tertiary amines, these amines do not escape in the cross-linking process but remain in the lacquer film ultimately obtained, where they may, for example, function as plasticizers.

In the case of blocked polyisocyanates according to the invention in which the cations are based on tertiary amines containing at least two blocked isocyanate groups, the amine is split off in the process of heat curing, but then takes part in the cross-linking reaction as a blocked polyisocyanate.

The invention is further illustrated but is not intended to be limited by the following examples in which all parts and percentages are by weight unless otherwise specified.

EXAMPLES

EXAMPLE 1

116.6 g (1.34 mole) of butanoneoxime and 0.2 g of tin-II-octoate were added to 400 g (2 mole of NCO) of an isocyanurate-containing polyisocyanate based on 1,6-diisocyanatohexane and containing less than 0.7% of free 1,6-diisocyanatohexane and the mixture was heated to 100° C. The isocyanate content was determined titrimetrically after 2 hours (isocyanate content=5.5%).

515 g (0.67 mole of NCO) of the partially blocked polyisocyanate were dissolved in 250 g of acetone. The resulting solution was added dropwise with stirring over a period of 90 minutes at 10 to 20° C. to a solution of 28.1 g (0.67 mole) of cyanamide and 59.6 g (0.67 mole) of N,N-dimethylaminoethanol is 50 g of acetone. 600 g of water were added after the isocyanate band at 2260 $cm^{-1}$ had disappeared from the IR spectrum. Nitrogen was passed through the clear solution at 60° to 70° C. until no more acetone could be detected in the distillate.

The solution had a solids content of 50% and a blocked isocyanate group content (calculated as NCO) of 4.7%. The dispersed product contained 1.1 milliequivalents/g of anionic cyanurea groups, based on solids.

EXAMPLE 2

75.7 g (0.67 mole) of epsilon-caprolactam and 0.1 g of tin-II-octoate were added to 200 g (1 mole of NCO) of the isocyanurate-containing polyisocyanate of Example 1 and the mixture was heated to 120° C. The isocyanate content was determined titrimetrically after 2 hours (isocyanate content=5%).

250 g (0.3 mole of NCO) of the partially blocked polyisocyanate were dissolved in 100 g of tetrahydrofuran and added dropwise to a mixture of 12.5 g (0.3 mole) of cyanamide and 26.5 g (0.3 mole) of dimethylaminoethanol in 20 g of tetrahydrofuran as solvent within 20 minutes at 10° to 20° C. 250 g of water were added when the isocyanate band at 2260 $cm^{-1}$ had disappeared from the IR spectrum. Nitrogen was passed through the clear solution at 80° C. until no more tetrahydrofuran could be detected in the distillate.

The solution, which has a solids content of 53%, contained 4.7% of blocked isocyanate groups (calculated as NCO). The dispersed product contains 1.0 milliequivalents/g of anionic cyanurea groups.

EXAMPLE 3 (Use)

100 g of an aqueous solution having a solids content of 31% of a polyhydroxypolyacrylate based on hydroxyethyl methacrylate, styrene, methyl methacrylate, n-butyl-acrylate and acrylic acid in ratios by weight of 4:2:2:2:1 neutralized with ammonia were mixed with 100 g of the solution from Example 1. A stable, somewhat milky solution was obtained.

After application to an untreated sheet steel, a glossy, firmly adhering coating was obtained after 30 minutes at 150° to 160° C. This coating showed no signs of softening after 16 hours in water or after 5 minutes in acetone.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a coated substrate which comprises coating said substrate with a mixture comprising (I) a water soluble or dispersible blocked polyissocyanate which comprises (a) a statistical average per molecule of at least one structural nit corresponding to the formula

B—CO—NH— wherein B stands for a group obtainable by removal of the acidic hydrogen atom from a monofunctional blocking agent for organic isocyanates and (b) a structural unit corresponding to the formula $$-NH-CO-\overset{\theta}{N}-CN$$

in a quantity sufficient to ensure the solubility or dispersibility of said blocked polyisocyanate in water, said blocked polyisocyanate containing a statistical average of at least two structural units corresponding to the formulas shown under (a) and (b) per molecule, and (II) an aqueous solution or dispersion of an organic compound containing least two isocyanate-reactive groups and subsuquently curing the coating by heat .

2. The process of claim 1 wherein said blocked polyisocyanate comprises (a) statistical average of at least two blocked isocyanate groups per molecule and (b) about 0.3 to 3.5 milliequivalents of anionic structural units per gram of solids.

3. The process of claim 1 wherein the counter ions to the anionic structural units (b) are ammonium groups obtainable by the addition of a proton to a tertiary amine.

4. The process of claim 2 wherein the counter ions to the anionic structural units (b) are ammonium groups obtainable by the addition of a proton to a tertiary amine.

5. The process of claim 3 wherein said tertiary amine has a molecular weight of 59 to about 1000 and contains at least one tertiary amino group in which all of the substituents on the tertiary amine nitrogen are aliphatic substituents.

6. The process of claim 4 wherein said tertiary amine has a molecular weight of 59 to about 1000 and contains at least one tertiary amino group in which all of the substituents on the tertrary amine nitrogen are aliphatic substituents.

7. The process of claim 5 wherein said tertiary amine additionally contains at least two blocked isocyante groups corresponding to the formula

B′—CO—NH wherein B′ corresponds to the definition of B but may be different than B.

8. The process of claim 6 wherein said tertiary amine additionally contains at least two blocked isocyanate groups corresponding to the formula

B′—CO—NH— wherein B′, corresponds to the definition of B but may be different than B.

* * * * *